United States Patent
Ma et al.

(10) Patent No.: US 9,928,446 B2
(45) Date of Patent: Mar. 27, 2018

(54) AUGMENTED AUTOMATIC DEFECT CLASSIFICATION

(71) Applicant: Dongfang Jingyuan Electron Limited, Beijing (CN)

(72) Inventors: Weimin Ma, Beijing (CN); Xiaomei Wu, Beijing (CN); Zhaoli Zhang, Beijing (CN)

(73) Assignee: Dongfang Jingyuan Electron Limited, Beijing (CN)

( * ) Notice: Subject to any disclaimer, the term of this patent is extended or adjusted under 35 U.S.C. 154(b) by 0 days.

(21) Appl. No.: 15/285,955

(22) Filed: Oct. 5, 2016

(65) Prior Publication Data

US 2018/0018542 A1   Jan. 18, 2018

Related U.S. Application Data

(63) Continuation of application No. PCT/CN2016/097168, filed on Aug. 29, 2016.

(30) Foreign Application Priority Data

Jul. 13, 2016   (CN) .......................... 2016 1 0551876

(51) Int. Cl.
*G06K 9/00* (2006.01)
*G06K 9/62* (2006.01)
(Continued)

(52) U.S. Cl.
CPC ......... *G06K 9/6267* (2013.01); *G06K 9/4604* (2013.01); *G06T 7/001* (2013.01);
(Continued)

(58) Field of Classification Search
CPC ..... G06K 9/6267; G06K 9/4604; G06T 7/001
See application file for complete search history.

(56) References Cited

U.S. PATENT DOCUMENTS 8,204,297 B1   6/2012 Xiong et al.
2007/0230770 A1 * 10/2007 Kulkarni ............. G06F 17/5045
382/149

(Continued)

FOREIGN PATENT DOCUMENTS

| CN | 1494558 A | 5/2004 |
| CN | 103748670 A | 4/2014 |
| CN | 104568979 A | 4/2015 |

*Primary Examiner* — David F Dunphy
(74) *Attorney, Agent, or Firm* — Young Basile Hanlon & MacFarlane, P.C.

(57) ABSTRACT

A method for managing defects for an augmented automatic defect classification (ADC) process is disclosed. The method includes receiving a defect record based on an inspection of a target specimen; extracting, from a design database, relevant design data associated with a patch surrounding a location of a defect from the defect record; performing, by a processor, lithographic simulation on the relevant design data associated with the patch to determine a context patch; comparing, by the processor, the context patch with an image of the defect from the defect record to determine whether there exists a match between the context patch and the image of the defect; and defining the defect as a systematic defect based on a determination that there exists a match between the context patch and the image of the defect.

20 Claims, 5 Drawing Sheets

(51) Int. Cl.
  *G06T 7/00*   (2017.01)
  *G06K 9/46*   (2006.01)
  *G01N 21/95*   (2006.01)
  *G01N 23/225*   (2018.01)

(52) U.S. Cl.
  CPC ..... *G01N 21/9501* (2013.01); *G01N 23/2251* (2013.01); *G01N 2201/12* (2013.01); *G01N 2223/401* (2013.01); *G01N 2223/6116* (2013.01); *G01N 2223/646* (2013.01); *G06T 2207/30148* (2013.01)

(56) References Cited

U.S. PATENT DOCUMENTS

2009/0136121 A1* 5/2009 Nakagaki .............. G06T 7/0006
  382/149
2013/0287287 A1* 10/2013 Lin ......................... G06K 9/48
  382/144
2015/0139531 A1* 5/2015 Hirai ....................... G06T 7/001
  382/149
2015/0221076 A1   8/2015 Gao et al.
2016/0012579 A1* 1/2016 Shi .......................... G06T 7/001
  382/149
2017/0169554 A1* 6/2017 Karlinsky ............... G06T 7/001

* cited by examiner

AUGMENTED AUTOMATIC DEFECT CLASSIFICATION

CROSS REFERENCE TO RELATED APPLICATION(S)

This application claims priority to Chinese application No. 201610551876.4 filed on Jul. 13, 2016 and is a continuation of International patent application No. PCT/CN2016/097168 filed on Aug. 29, 2016, the contents of both of which are incorporated herein by reference in their entireties.

TECHNICAL FIELD

This disclosure relates to managing defects for an augmented automatic defect classification (ADC) process using simulation techniques such as, for example, lithographic simulation.

BACKGROUND

Automatic Defect Classification (ADC) has been widely used in semiconductor manufacturing. With the technology progressing into finer resolutions such as beyond 20 nm, increasing number of defects can be caused by various system conditions, e.g., process variation, and OPC techniques. The ever-increasing systematic defects can lead to lower performances.

SUMMARY

Disclosed herein is a method for augmented automatic defect classification (ADC) with lithographic simulation. The method includes receiving a defect record based on an inspection of a target specimen; extracting, from a design database, relevant design data associated with a patch surrounding a location of a defect from the defect record; performing, by a processor, lithographic simulation on the relevant design data associated with the patch to determine a context patch; comparing, by the processor, the context patch with an image of the defect from the defect record to determine whether there exists a match between the context patch and the image of the defect; and defining the defect as a systematic defect based on a determination that there exists a match between the context patch and the image of the defect.

Also disclosed herein is a non-transitory computer-readable medium storing a set of instructions which when executed by a processor of a computer system become operational with the processor for managing defects for an augmented automatic defect classification (ADC) process. The non-transitory computer readable medium comprises instructions for receiving a defect record based on an inspection of a target specimen; instructions for extracting, from a design database, relevant design data associated with a patch surrounding a location of a defect from the defect record; instructions for performing lithographic simulation on the relevant design data associated with the patch to determine a context patch; instructions for comparing the context patch with an image of the defect from the defect record to determine whether there exists a match between the context patch and the image of the defect; and instructions for defining the defect as a systematic defect based on a determination that there exists a match between the context patch and the image of the defect.

Also disclosed herein is a system for managing defects for an augmented automatic defect classification (ADC) process. The system includes a processor and a memory coupled to the processor, the memory configured to store a set of instructions which when executed by the processor become operational with the processor to receive a defect record based on an inspection of a target specimen; extract, from a design database, relevant design data associated with a patch surrounding a location of a defect from the defect record; perform lithographic simulation on the relevant design data associated with the patch to determine a context patch; compare the context patch with an image of the defect from the defect record to determine whether there exists a match between the context patch and the image of the defect; and define the defect as a systematic defect based on a determination that there exists a match between the context patch and the image of the defect.

Details of these implementations, modifications of these implementations, and additional implementations are described below.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

DETAILED DESCRIPTION

Defect classification, including automatic defect classification (ADC), has been widely used in semiconductor manufacturing. In defect classification, a label can be assigned to a defect after analyzing the characteristics of a defect image associated with the defect. By assigning a correct label to a detected defect, pre-defined course of action can be quickly implemented to handle the defect, the wafer, or the reticle on the production line. Further, analysis of defects based on classifications can guide the formulation of remedial plan to improve the process and yield.

During the automatic defect classification (ADC) process, as the technology progresses beyond the 20 nm design resolution, there is an increasing number of defects, which are often caused by system conditions, such as process variation, interactions between the design and process, and advanced lithographic techniques (e.g., OPC). Accordingly, defects discerned by the ADC process can be classified into categories such as systematic defects and random defects. Systematic defects (e.g., artifacts), as they are often caused by resolution enhancement technologies, can be harmless and might not have a fatal impact on the manufacturing process. However, systematic defects can be fatal when, for example, they are caused by the design of geometry that the manufacturing process could not resolve. Random defects, on the other hand, are often caused by particles (e.g., dusts on the wafer), inhomogeneities or irregularities. A random defect can be harmless (e.g., when a random defect affects a part of a chip that does not have any electronic significance), or fatal (e.g., when a random defect open or short a circuit). In addition to system and random defects, other types of defects can also be classified.

According to implementations of this disclosure, an augmented ADC process with lithographic simulation is used to supplement the systematic defect information to the ADC process, and to guide the ADC process to assign the correct classification to the defects. As will be described in further details below, an inspection is performed on a wafer or a reticle ("target specimen") to generate the defect record. The defect location of a defect can be extracted from the defect record, and a database clip including the corresponding relevant design data can be extracted from the design database for a patch surrounding the defect location. Lithographic simulation can be performed on the database clip to produce a context patch, which will be compared with the defect image for identifying a systematic defect. In addition to systematic defects, other types of defects can also be identified accordingly.

Figure 1:
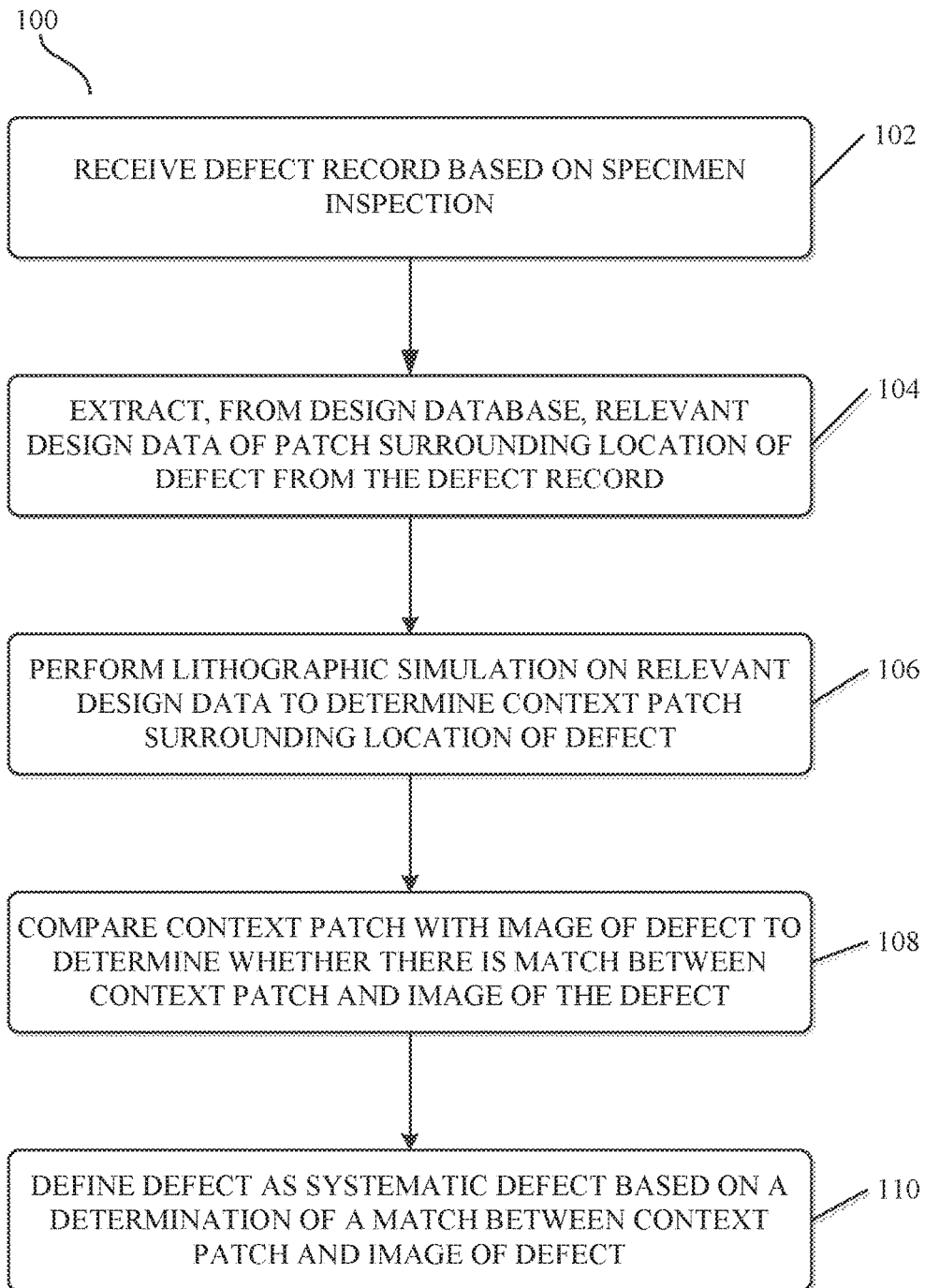
FIG. 1 is a diagram showing an example process of augmented automatic defect classification (ADC) with lithographic simulation.

FIG. 1 is a diagram showing an example process 100 of augmented automatic defect classification (ADC) with lithographic simulation. Augmented ADC process 100 depicted in FIG. 1 may be performed by software modules (e.g., instructions or code) executed by a processor of a computer system, by hardware modules of the computer system, or combinations thereof. One or more operations described herein can be incorporated into, for example, wafer or reticle inspection products and be used by a semiconductor manufacturer.

At operation 102, a defect record is received based on an inspection of a target specimen. The target specimen can include, for example, a wafer or a reticle. The inspection can include, for example, an optical or an E-beam inspection. The defect record can be part of an inspection report, and can include one or more defects. Each defect can include, for example, location and image information. The location can include data about the location of the defect, such as layer information and coordinates. The defect image and/or location can be extracted from the defect record.

At operation 104, relevant design data of a patch surrounding the location of a defect is extracted from a design database. Design database can include, for example, at least one design database file corresponding to the design of the target specimen, such as a wafer or a reticle, and can include data such as chip blueprints and polygon descriptions, etc. The relevant design data can be extracted as a database clip, which contains relevant data of a patch surrounding the defect location. The relevant design data can include any data associated with the design of a wafer or a reticle, which can include, for example, physical data (e.g., size), geometry data (e.g., shape or layout), technical data, layer data, or any combination thereof.

At operation 106, lithographic simulation is performed on the relevant design data to determine a context patch surrounding the location of the defect. For example, lithographic simulation can be run on the database clip to produce the context patch surrounding the defect location. The context patch includes a simulated image, which is basically a simulated database image based on the calibrated models of the lithographic process. The context patch can also include data such as circuits, routes, and other data generated or rendered using the lithographic process.

At operation 108, the context patch is compared with the image of the defect to determine whether there is a match between the context patch and the image of the defect. The context patch can be compared with the image of the defect by, for example, subtracting one image from another after aligning the two. The comparison can also be performed using a defect detection algorithm, which can be determined based on the specific requirements of the application.

As discussed above, the inspection can be an optical inspection or an E-beam inspection. When the inspection is an optical inspection, the context patch can be compared with an optical image of the defect (from the optical inspection), which can be similar to a die-to-database inspection. When the inspection is an E-beam inspection, a contour of the context patch can be compared with a contour of a SEM image (from the E-beam inspection) of the defect. In some implementations, the respective contours can be extracted, and then compared.

When the simulated image (of the context patch) matches with the defect image, it shows that the defect image can be re-created from the design database using the simulation process. This would indicate that the defect is more likely to have been caused by system factors (such as OPC or process variation etc.), not random factors (such as dusts).

At operation 110, the defect is defined as a systemic defect based on a determination that there exists a match between the context patch and the image of the defect. Responsive to the match result, the defect can be classified as either a systematic defect or a non-systematic defect. When it is determined that there does not exist a match between the context patch and the image of the defect, the defect will not be classified as a systematic defect. In some implementations, the defect can be classified as a non-systematic defect (e.g., a random defect or another type of defect), or be given a specific label based on the context and defect information, according to other aspects of the ADC decision making.

Using the operations described above, the original ADC process is augmented to take into consideration of the systematic defect information when processing the defects. The systematic defect information (or non-systematic defect information), along with other relevant information (such as context information), can be used to augment the ADC process during its decision making, as discussed above. For example, the information included in the context patches can also be used by augmented ADC process in other ways. In one example, certain defects can be pre-classified or eliminated using a predetermined rule. In another example, the system defects can be automatically classified using a predetermined rule during the augmented ADC process. When the ADC process is augmented (or assisted) by lithographic simulation, a classifier in the ADC process would have knowledge of, for example, where a defect is located on the circuits and the types of circuits, allowing it to make an informed decision on the effect of the defect on the circuits, and to correctly classify the defect. In addition, the augmented ADC process can be applied to scenarios beyond the examples given above, and can be used to classify all categories of defects (e.g., shapes and shades), based on, for example, information on the surroundings of the defects provided by the lithographic simulation.

Figure 2:
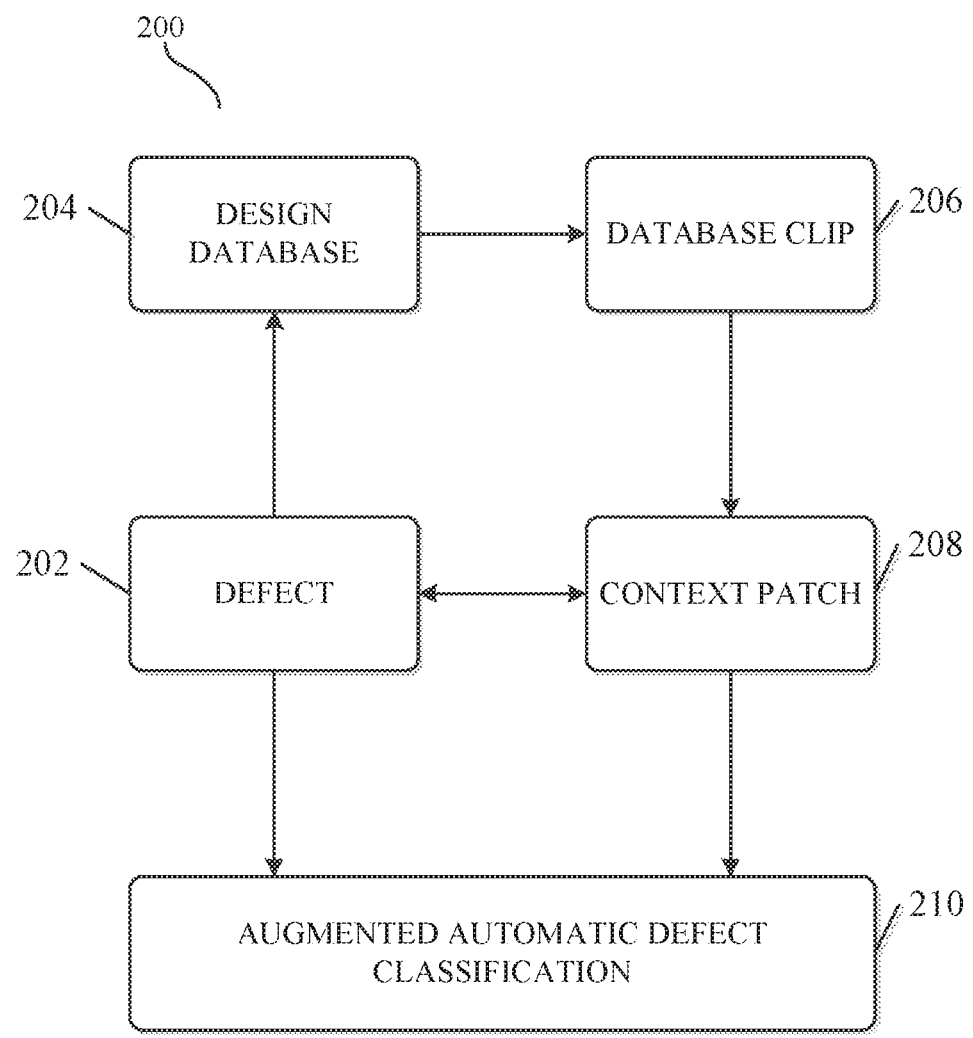
FIG. 2 is a diagram showing an example augmented ADC process with lithographic simulation.

FIG. 2 is a diagram showing an example augmented ADC process 200 with lithographic simulation. The process 200 depicted in FIG. 2 may be performed by software modules (e.g., instructions or code) executed by a processor of a computer system, by hardware modules of the computer system, or combinations thereof.

According to the example illustrated in FIG. 2, augmented ADC process 200 includes extracting from the design database 204, relevant design data (database clip 206) associated with a patch surrounding a location of a defect 202. Defect 202 can be obtained from, for example, a defect record as a result of an inspection (such as an optical or an E-beam inspection) of a target specimen (such as a wafer or a reticle). As discussed above, lithographic simulation can be performed on the relevant design data (database clip 206) associated with the patch to determine the context patch 208. Subsequently, an image of defect 202 ("defect image") can be compared with the context patch 208, by augmented ADC 210, to determine whether there exists a match between the context patch and the defect image, and/or to classy the defect as a systematic defect or a non-systematic defect, among other things. In this way, the original ADC is augmented to take into consideration of the systematic defect information when processing the defects.

For example, the design database for a wafer or a reticle can be very large, and can include such as several hundreds or thousands of gigabytes of data, while the database clip containing the relevant design data associated with the patch surrounding the location of the defect 202 can be relatively small, and can include such as at around one or several megabytes of data. The size of the patch (or database clip 206) can vary based on, for example, the shape or size of the defect. In one example, the patch can have a width and height of 32×32 or 64×64.

Figure 3:
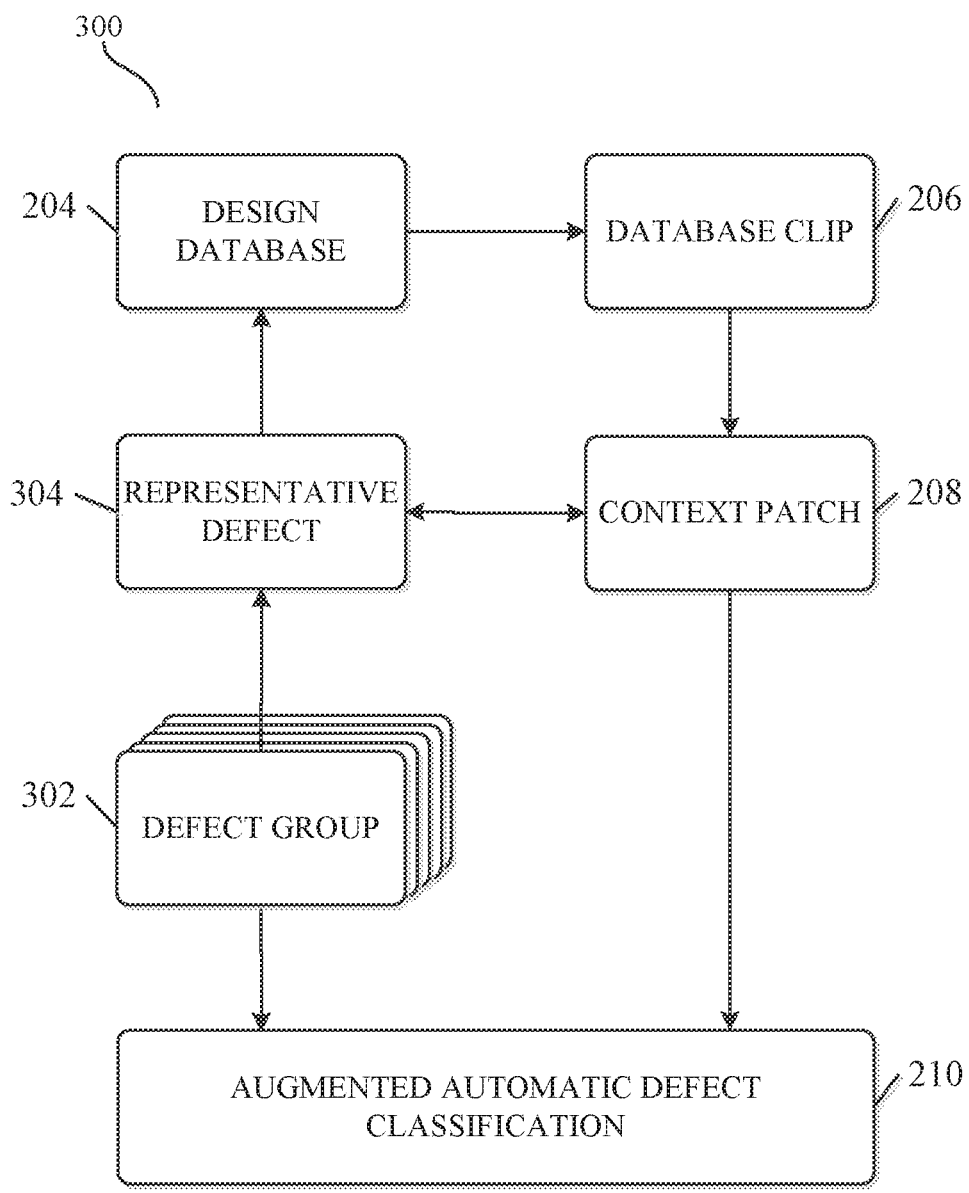
FIG. 3 is a diagram showing another example augmented ADC process with lithographic simulation.

FIG. 3 is a diagram showing another example augmented ADC process 300 with lithographic simulation. Process 300 depicted in FIG. 3 may be performed by software modules (e.g., instructions or code) executed by a processor of a computer system, by hardware modules of the computer system, or combinations thereof.

Defects can be grouped based on image similarity. Augmented ADC process 300 differs from augmented ADC process 200 in that defects from the defect record are sorted into groups. For example, all the defects in a defect group (e.g., defect group 302) can have the same or similar images. Each defect group can have a representative defect 304, which can be a randomly selected defect, or a designated one based on one or more predetermined rules. For example, a new defect can be compared with an image of the representative defect 304 ("representative defect image") of each defect group to determine the defect group the new defect belongs to.

Once all the defects from the defect record have been processed and sorted into groups, the representative defect image of a group can be compared (e.g., at operation 108 of FIG. 1) with the context patch 208 corresponding to the representative defect of that group (e.g., determined at operation 106 of FIG. 1). Rather than comparing each defect image with a context patch, the representative defect image can be compared, for the group, with its corresponding context patch, which would greatly reduce the computational work. The comparison result can be used, for example, by the augmented ADC 210, which will process the same information for each defect within the same group. For example, when a representative defect image of a defect group is determined to match the context patch generated for that defect group, all of the defects within the group can be classified as systematic defects without repeating the operations.

In the illustrated example, augmented ADC process 300 includes extracting from the design database 204, relevant design data (database clip 206) associated with a patch surrounding a location of the representative defect 304 of defect group 302. As discussed above, lithographic simulation can be performed on the relevant design data (database clip 206) associated with the patch to determine the context patch 208. Subsequently, the representative defect image of defect group 302 can be compared with the context patch 208, by Augmented ADC 210, to determine whether there exists a match between the context patch and the representative defect image and/or to classy all of the defects of the defect group as systematic defects or non-systematic defects, among other things.

Figure 4:
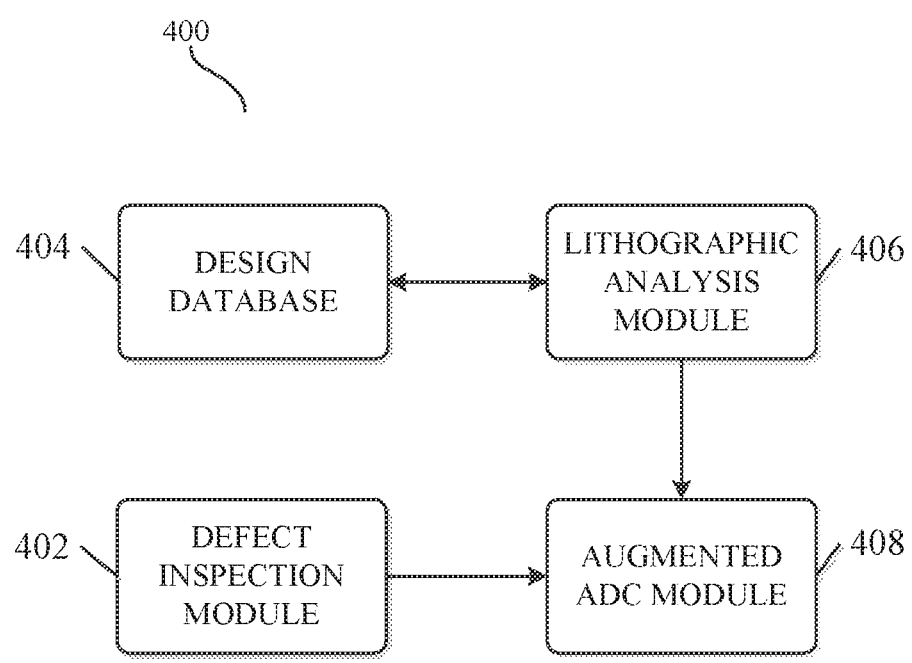
FIG. 4 is a diagram of an example augmented ADC system.

FIG. 4 is a diagram of an example augmented automatic defect classification (ADC) system 400. Aspects of the disclosure, e.g., operations of processes 100, 200, 300 can be implemented as software and/or hardware modules in the augmented ADC system 400. For example, augmented ADC system 400 can include an apparatus such as a computing device, which can be implemented by any configuration of one or more computers, such as a microcomputer, a mainframe computer, a super computer, a general-purpose computer, a special-purpose/dedicated computer, an integrated computer, a database computer, a remote server computer, a personal computer, or a computing service provided by a computing service provider, e.g., a web host, or a cloud service provider. In some implementations, the computing device can be implemented in the form of multiple groups of computers that are at different geographic locations.

In the illustrated example, augmented ADC system 400 can include a defect inspection module 402, a design database 404, a lithographic analysis module 406, and an augmented ADC module 408. Defect inspection module 402 can be configured to perform an inspection (such as an optical or an E-beam inspection) on a target specimen (such as a wafer or a reticle), and generate an inspection report including a defect record. As discussed above, the defect record can include a list of defects, and each defect can include image and location information. In some implementations, defects can be sorted into groups and a representative defect of a group can be used for comparison instead of each individual defect, as discussed in FIG. 3.

Design database 404 can be any database that stores the design data of the wafer or reticle. As discussed previously, relevant data of a patch surrounding a defect location (herein "database clip") can be extracted and retrieved from the design database 404.

Lithographic analysis module 406 can perform lithographic simulation on the database clip to generate the context patch. As discussed above, the context patch can include various context information surrounding the defect location, such as a simulated database image as a result of the lithographic process.

Augmented ADC module 408 can use the context patches (generated by lithographic analysis module 406) and defect information (generated by defect inspection module 402) for its decision making. For example, augmented ADC module 408 can compare a defect image and a corresponding context patch: when there is a match, the defect is identified as a systematic defect. In some implementations, an image of the representative defect of a group can be compared with the corresponding context patch: when there is a match, the group (and all defects of the group) is identified as a systematic defect (or systematic defects). The information included in the context patches can also be used by augmented ADC module 408 in other ways, such as, for example, certain defects can be pre-classified or eliminated using a predetermined rule.

Figure 5:
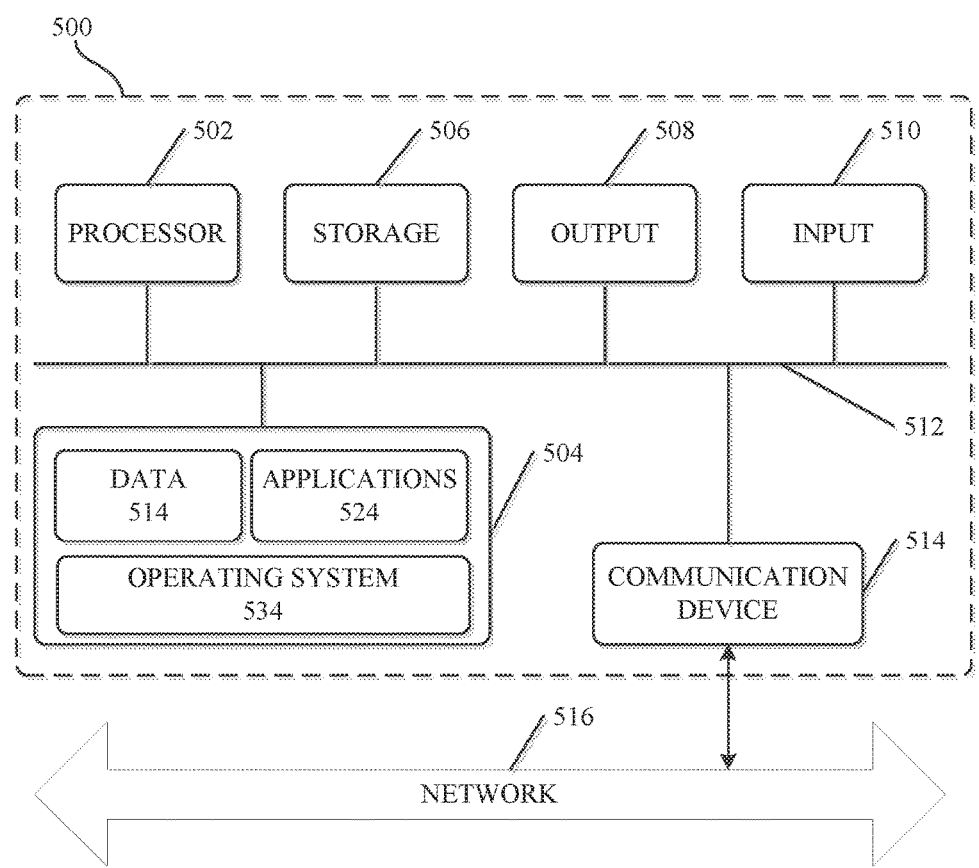
FIG. 5 is a diagram of an example augmented ADC system in which aspects of the disclosure can be implemented.

FIG. 5 is a diagram of an example augmented automatic defect classification (ADC) system 500 in which aspects of the disclosure can be implemented. For example, augmented ADC system 500 can include, for example, an apparatus such as a computing device. In some implementations, the computing device can be implemented by any configuration of one or more computers, such as a microcomputer, a mainframe computer, a super computer, a general-purpose computer, a special-purpose/dedicated computer, an integrated computer, a database computer, a remote server computer, a personal computer, or a computing service provided by a computing service provider, e.g., a web host, or a cloud server. In some implementations, the computing device can be implemented in the form of multiple groups of computers that are at different geographic locations and can or cannot communicate with one another, such as by way of a network. While certain operations can be shared by multiple computers, in some implementations, different computers are assigned different operations.

The computing device can have an internal configuration of hardware including processor 502 and memory 504. Processor 502 can include at least one processing unit such as a central processing unit (CPU) or any other type of device, or multiple devices, capable of manipulating or processing information now-existing or hereafter developed. Although the examples herein can be practiced with a single processor as shown, advantages in speed and efficiency can be achieved using more than one processor. For example, processor 502 can be distributed across multiple machines or devices (each machine or device having one or more of processors) that can be coupled directly or across a local area or other network. Memory 504 can be a random access memory device (RAM), a read-only memory device (ROM), an optical disc, a magnetic disc, or any other suitable type of storage device. In some implementations, memory 504 can be distributed across multiple machines or devices such as network-based memory or memory in multiple machines performing operations that can be described herein as being performed using a single computer or computing device for ease of explanation. In some implementations, memory 504 can store codes and data that can be accessed by processor 502 using a bus. For example, memory 504 can include data 5042 that can be accessed by processor 502 using bus 512.

Memory 504 can also include operating system 5046 and installed applications 5044, applications 5044 including programs that permit processor 502 to implement instructions to generate control signals for performing functions of augmented ADC system 500 as described herein. The instructions can also include processing defect information for classifications that are not part of the ADC system, such as producing context information that can be used to generate systematic defect labels by the ADC system. Augmented ADC system 500 can also include a secondary, additional or external storage 506, for example, a memory card, a flash drive, an external hard drive, an optical drive, or any other form of computer readable medium. In some implementations, applications 5044 can be stored in a whole or in part in storage 506 and loaded into memory 504 as needed for processing.

Augmented ADC system 500 can include one or more output devices, such as output 508. Output 508 can be implemented in various ways, for example, it can be a display that can be coupled to augmented ADC system 500 and configured to display a rendering of video data. Output 508 can be any device transmitting a visual, acoustic, or tactile signal to the user, such as a display, a touch sensitive device (e.g., a touch screen), a speaker, an earphone, a light-emitting diode (LED) indicator, or a vibration motor. If output 508 is a display, for example, it can be a liquid crystal display (LCD), a cathode-ray tube (CRT), or any other output device capable of providing visible output to an individual. In some cases, an output device can also function as an input device—a touch screen display configured to receive touch-based input, for example.

Output 508 can alternatively or additionally be formed of a communication device for transmitting signals and/or data. For example, output 508 can include a wired mean for transmitting signals or data from augmented ADC system 500 to another device. For another example, output 508 can include a wireless transmitter using a protocol compatible with a wireless receiver to transmit signals from augmented ADC system 500 to another device.

Augmented ADC system 500 can include one or more input devices, such as input 510. Input 510 can be implemented in various ways, such as a keyboard, a numerical keypad, a mouse, a microphone, a touch sensitive device (e.g., a touch screen), a sensor, or a gesture-sensitive input device. Any other type of input device, including an input device not requiring user intervention, is possible. For example, input 510 can be a communication device such as a wireless receiver operating according to any wireless protocol for receiving signals. Input 510 can output signals or data, indicative of the inputs, to augmented ADC system 500, e.g., along bus 512.

Optionally, augmented ADC system 500 can be in communication with another device using a communication device, such as communication device 514, via a network, such as network 516. Network 516 can be one or more communications networks of any suitable type in any combination, including, but not limited to, networks using Bluetooth communications, infrared communications, near field connections (NFC), wireless networks, wired networks, local area networks (LAN), wide area networks (WAN), virtual private network (VPN), cellular data networks and the Internet. Communication device 514 can be implemented in various ways, such as a transponder/transceiver device, a modem, a router, a gateway, a circuit, a chip, a wired network adapter, a wireless network adapter, a Bluetooth adapter, an infrared adapter, an NFC adapter, a cellular network chip, or any suitable type of device in any combination that is coupled to augmented ADC system 500 using bus 512 to provide functions of communication with network 516.

Augmented ADC system 500 can communicate with a wafer or reticle inspection equipment. For example, the augmented ADC system 500 can be coupled to one or more wafer or reticle inspection equipment configured to generate wafer or reticle inspection results (e.g., defect records or reports).

Augmented ADC system 500 (and algorithms, methods, instructions etc. stored thereon and/or executed thereby) can be realized in hardware including, for example, intellectual property (IP) cores, application-specific integrated circuits (ASICs), programmable logic arrays, optical processors, programmable logic controllers, microcode, firmware, microcontrollers, servers, microprocessors, digital signal processors or any other suitable circuit. In the claims, the term "processor" should be understood as encompassing any the foregoing, either singly or in combination. The terms "signal" and "data" are used interchangeably. Further, portions of augmented ADC system 500 do not necessarily have to be implemented in the same manner.

In some implementations, augmented ADC system 500 can be implemented using general purpose computers/processors with a computer program that, when executed, carries out any of the respective methods, algorithms and/or instructions described herein. In addition or alternatively, for example, special purpose computers/processors can be utilized which can contain specialized hardware for carrying out any of the methods, algorithms, or instructions described herein.

While the disclosure has been described in connection with certain embodiments and implementations, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for managing defects for an augmented automatic defect classification (ADC) process, comprising:
   receiving a defect record based on an inspection of a target specimen;
   extracting, from a design database, relevant design data associated with a patch surrounding a location of a defect from the defect record;
   performing, by a processor, lithographic simulation on the relevant design data associated with the patch to determine a context patch;
   comparing, by the processor, the context patch with an image of the defect from the defect record to determine whether there exists a match between the context patch and the image of the defect; and
   defining the defect as a systematic defect based on a determination that there exists a match between the context patch and the image of the defect.

2. The method of claim 1, further comprising:
   defining the defect as a non-systematic defect based on a determination that there does not exist a match between the context patch and the image of the defect.

3. The method of claim 1, further comprising sorting the defect into a defect group selected from a plurality of defect groups based on similarity of the image of the defect to a representative defect image of the defect group.

4. The method of claim 3, wherein extracting, from a design database, relevant design data associated with a patch surrounding a location of a defect from the defect record comprises extracting, from the design database, relevant design data associated with a patch surrounding a location of the representative defect of the defect group from the defect record.

5. The method of claim 3, wherein comparing, by the processor, the context patch with an image of the defect from the defect record to determine whether there exists a match between the context patch and the image of the defect comprises:
   comparing the representative defect image of the defect group with the context patch.

6. The method of claim 5, wherein defining the defect as a systematic defect based on a determination that there exists a match between the context patch and the image of the defect comprises:
   defining each defect in the defect group as a systematic defect based on a determination that there exists a match between the context patch and the representative image of the defect group.

7. The method of claim 1, wherein the augmented automatic defect classification (ADC) process is performed for the defect record taking into consideration the systematic defects during decision making.

8. The method of claim 1, wherein the system defects are automatically classified using a predetermined rule during the augmented automatic defect classification (ADC) process.

9. The method of claim 1, wherein the target specimen comprises a wafer or a reticle.

10. The method of claim 1, wherein the inspection comprises an optical inspection or an E-beam inspection, and wherein comparing the context patch and the image of the defect to determine whether there exists a match between the context patch and the image of the defect comprises:
    comparing a contour of the context patch with a contour of a SEM image of the defect when the inspection comprises an E-beam inspection; and
    comparing the context patch with an optical image of the defect when the inspection comprises an optical inspection.

11. A non-transitory computer-readable medium storing a set of instructions which when executed by a processor of a computer system become operational with the processor for managing defects for an augmented automatic defect classification (ADC) process, the non-transitory computer-readable medium comprising:
    instructions for receiving a defect record based on an inspection of a target specimen;
    instructions for extracting, from a design database, relevant design data associated with a patch surrounding a location of a defect from the defect record;
    instructions for performing lithographic simulation on the relevant design data associated with the patch to determine a context patch;
    instructions for comparing the context patch with an image of the defect from the defect record to determine whether there exists a match between the context patch and the image of the defect; and
    instructions for defining the defect as a systematic defect based on a determination that there exists a match between the context patch and the image of the defect.

12. The non-transitory computer-readable medium of claim 11, further comprising:
    instructions for sorting the defect into a defect group selected from a plurality of defect groups based on similarity of the image of the defect to a representative defect image of the defect group;
    instructions for extracting, from the design database, relevant design data associated with a patch surrounding a location of the representative defect of the defect group from the defect record;
    instructions for comparing the representative defect image of the defect group with the context patch; and
    instructions for defining each defect in the defect group as a systematic defect based on a determination that there exists a match between the context patch and the representative image of the defect group.

13. The non-transitory computer-readable medium of claim 11, wherein the automatic defect classification (ADC) process is performed for the defect record taking into consideration the systematic defects during decision making.

14. The non-transitory computer-readable medium of claim 11, wherein the system defects are automatically classified using a predetermined rule during the automatic defect classification (ADC) process.

15. The non-transitory computer-readable medium of claim 11, wherein the target specimen comprises a wafer or a reticle.

16. The non-transitory computer-readable medium of claim 11, wherein the inspection comprises an optical inspection or an E-beam inspection, and wherein the instructions for comparing the context patch and the image of the defect to determine whether there exists a match between the context patch and the image of the defect comprises:
   instructions for comparing a contour of the context patch with a contour of a SEM image of the defect when the inspection comprises an E-beam inspection; and
   instructions for comparing the context patch with an optical image of the defect when the inspection comprises an optical inspection.

17. A system for managing defects for an augmented automatic defect classification (ADC) process, the system comprising:
   a processor; and
   a memory coupled to the processor, the memory configured to store a set of instructions which when executed by the processor become operational with the processor to:
      receive a defect record based on an inspection of a target specimen;
      extract, from a design database, relevant design data associated with a patch surrounding a location of a defect from the defect record;
      perform lithographic simulation on the relevant design data associated with the patch to determine a context patch;
      compare the context patch with an image of the defect from the defect record to determine whether there exists a match between the context patch and the image of the defect; and
      define the defect as a systematic defect based on a determination that there exists a match between the context patch and the image of the defect.

18. The system of claim 17, wherein the memory is further configured to store a set of instructions which when executed by the processor become operational with the processor to:
   sort the defect into a defect group selected from a plurality of defect groups based on similarity of the image of the defect to a representative defect image of the defect group;
   extract, from the design database, relevant design data associated with a patch surrounding a location of the representative defect of the defect group from the defect record;
   compare the representative defect image of the defect group with the context patch; and
   define each defect in the defect group as a systematic defect based on a determination that there exists a match between the context patch and the representative image of the defect group.

19. The system of claim 17, wherein the target specimen comprises a wafer or a reticle.

20. The system of claim 17, wherein the inspection comprises an optical inspection or an E-beam inspection, and wherein the instructions to compare the context patch and the image of the defect to determine whether there exists a match between the context patch and the image of the defect comprise instructions to:
   compare a contour of the context patch with a contour of a SEM image of the defect when the inspection comprises an E-beam inspection; and
   compare the context patch with an optical image of the defect when the inspection comprises an optical inspection.

* * * * *